US006902397B2

(12) United States Patent
Farrell et al.

(10) Patent No.: US 6,902,397 B2
(45) Date of Patent: Jun. 7, 2005

(54) ENHANCED DENTAL HYGIENE SYSTEM WITH DIRECT UVA PHOTOEXCITATION

(75) Inventors: Lawrence W. Farrell, Cinncinnati, OH (US); Kevin G. Yost, Winnetka, IL (US); Chris Stvartak, Skokie, IL (US)

(73) Assignee: Sunstar Americas, Inc., Chicago, IL (US)

( * ) Notice: Subject to any disclaimer, the term of this patent is extended or adjusted under 35 U.S.C. 154(b) by 109 days.

(21) Appl. No.: 10/210,758

(22) Filed: Aug. 1, 2002

(65) Prior Publication Data

US 2004/0019990 A1 Feb. 5, 2004

(51) Int. Cl.[7] .............................. A61C 3/00; A46B 9/04
(52) U.S. Cl. ......................... 433/29; 15/22.1; 15/167.1
(58) Field of Search .................... 433/29, 215; 15/22.1, 15/105, 167.1

(56) References Cited

U.S. PATENT DOCUMENTS

| 2,397,757 | A | | 4/1946 | Schwedersky | |
|---|---|---|---|---|---|
| 2,688,971 | A | | 9/1954 | Daniels | |
| 3,261,978 | A | * | 7/1966 | Brenman | ...................... 15/105 |
| 3,667,454 | A | * | 6/1972 | Prince | .......................... 601/18 |
| 4,526,570 | A | | 7/1985 | Nakagawa | |
| 4,668,712 | A | | 5/1987 | Hino | |
| 4,779,173 | A | | 10/1988 | Carr | |

(Continued)

FOREIGN PATENT DOCUMENTS

| EP | 0 737 513 A1 | 10/1996 |
|---|---|---|
| EP | 0 743 029 A2 | 11/1996 |
| EP | 0 743 029 A3 | 7/1997 |
| EP | 0 927 544 B1 | 2/2003 |
| EP | 1 083 806 B1 | 8/2003 |
| JP | 3-251207 | 11/1991 |
| JP | 6-113920 | 4/1994 |
| JP | 2001-114658 | 4/2001 |

OTHER PUBLICATIONS

Biolase Technology Inc. Report, Kevin Yost, Ph.D., John O. Butler Company, Chicago, Illinois US, Sep. 10, 2001.
U.S. Government Printing Office via GPO Access, Code of Federal Regualtions: Title 21, vol. 1, "Listing of Color Additive Exempt from Certification", Apr. 1, 2001.
White Paper, "Evaluation of Self–Disinfecting and Self–Cleaning Brush Bristle Additives/Coatings", R.E. Baier, School of Dental Medicine, SUNY Buffalo, US, Sep. 2, 1999.
White Paper, "Evaluation of Dentifice–Activated Oral Health Devices and Self–Cleaning Brush Bristle Additives/Coatings", Joseph Zambon, Homer Reynolds, Robert Baier, Anne Meyer, and associates, no date.
Slide Presentation, "Overview of Current Commercial Semiconductor Photocatalysis", Soo–Keun Lee and Andrew Mills, Department of Pure & Applied Chemistry, University of Strathclyde, UK, no date.

*Primary Examiner*—John J Wilson
(74) *Attorney, Agent, or Firm*—Michael Best & Friedrich LLP (57) ABSTRACT

A device and a method for delivering UVA light to the mouth in which a photocatalytic agent is distributed in the mouth and a UVA light source is located contiguously to the head of the device so that the photocatalytic agent distributed in the mouth is efficiently activated by UVA light produced by the device. The UVA light delivery device of the invention may be, inter alia, a toothbrush, a tongue scraper, an interdental toothbrush, a denture brush, a flossing device, a dental hand tool, or a wand adapted exclusively to applying UVA light to photocatalyst coated surfaces.

9 Claims, 11 Drawing Sheets

U.S. PATENT DOCUMENTS

| | | | |
|---|---|---|---|
| 4,861,484 A | 8/1989 | Lichtin | |
| 4,966,759 A | 10/1990 | Robertson | |
| 4,983,379 A | 1/1991 | Schaeffer | |
| 5,030,090 A | * 7/1991 | Maeda et al. | 433/29 |
| 5,160,194 A | 11/1992 | Feldman | |
| 5,174,877 A | 12/1992 | Cooper | |
| 5,256,616 A | 10/1993 | Heller | |
| 5,294,315 A | 3/1994 | Cooper | |
| 5,306,143 A | 4/1994 | Levy | |
| 5,308,458 A | 5/1994 | Urwin | |
| 5,340,581 A | 8/1994 | Tseng | |
| 5,427,770 A | 6/1995 | Viccaro | |
| 5,516,492 A | 5/1996 | Dong | |
| 5,518,992 A | 5/1996 | Linkous | |
| 5,538,715 A | 7/1996 | Gaffar | |
| 5,547,823 A | 8/1996 | Murasawa | |
| 5,611,793 A | 3/1997 | Wilson | |
| 5,616,532 A | 4/1997 | Heller | |
| 5,622,501 A | 4/1997 | Levy | |
| 5,652,274 A | 7/1997 | Martin | |
| 5,658,148 A | 8/1997 | Neuberger | |
| 5,683,589 A | 11/1997 | De Lasa | |
| 5,686,064 A | 11/1997 | Gaffar | |
| 5,698,177 A | 12/1997 | Pratsinis | |
| 5,707,915 A | 1/1998 | Taoda | |
| 5,728,756 A | 3/1998 | Gaffar | |
| 5,755,867 A | 5/1998 | Chikuni | |
| 5,785,521 A | 7/1998 | Rizoiu | |
| 5,790,934 A | 8/1998 | Say | |
| 5,813,855 A | 9/1998 | Crisio | |
| 5,851,551 A | 12/1998 | Tseng | |
| 5,853,866 A | 12/1998 | Watanabe | |
| 5,854,169 A | 12/1998 | Heller | |
| 5,874,701 A | 2/1999 | Watanabe | |
| 5,880,067 A | 3/1999 | Linkous | |
| 5,894,620 A | 4/1999 | Polaert | |
| 5,903,951 A | 5/1999 | Ionta | |
| 5,906,834 A | 5/1999 | Tseng | |
| 5,994,268 A | 11/1999 | Linkous | |
| 5,998,431 A | 12/1999 | Tseng | |
| 6,013,372 A | 1/2000 | Hayakawa | |
| 6,026,828 A | 2/2000 | Altshuler | |
| 6,027,797 A | 2/2000 | Watanabe | |
| 6,029,304 A | 2/2000 | Hulke | |
| 6,034,152 A | 3/2000 | Burger | |
| 6,037,289 A | 3/2000 | Chopin | |
| 6,051,194 A | 4/2000 | Peill | |
| 6,063,343 A | 5/2000 | Say | |
| 6,090,489 A | 7/2000 | Hayakawa | |
| 6,093,676 A | 7/2000 | Heller | |
| 6,094,767 A | 8/2000 | Iimura | |
| 6,135,838 A | 10/2000 | Wang | |
| 6,136,186 A | 10/2000 | Gonzalez-Martin | |
| 6,139,803 A | 10/2000 | Watanabe | |
| 6,165,327 A | 12/2000 | Pappa | |
| 6,210,779 B1 | 4/2001 | Watanabe | |
| 6,211,112 B1 | 4/2001 | Ishibashi | |
| 6,214,195 B1 | 4/2001 | Yadav | |
| 6,221,259 B1 | 4/2001 | Kittrell | |
| 6,235,351 B1 | 5/2001 | DiMarzio | |
| 6,268,050 B1 | 7/2001 | Watanabe | |
| 6,277,346 B1 | 8/2001 | Murasawa | |
| 6,281,265 B1 | 8/2001 | Montgomery | |
| 6,290,496 B1 | 9/2001 | Azar et al. | |
| 6,294,246 B1 | 9/2001 | Watanabe | |
| 6,294,247 B1 | 9/2001 | Watanabe | |
| 6,318,996 B1 | 11/2001 | Melikechi et al. | |
| 2003/0101526 A1 | 6/2003 | Hilscher et al. | |
| 2003/0104340 A1 | 6/2003 | Clemans | |
| 2004/0048224 A1 | 3/2004 | Black | |
| 2004/0053190 A1 | 3/2004 | Lin | |

* cited by examiner

ENHANCED DENTAL HYGIENE SYSTEM WITH DIRECT UVA PHOTOEXCITATION

BACKGROUND OF THE INVENTION

This invention relates generally to dental hygiene systems and methods for enhancing the toothbrushing process. More particularly this invention relates to a dental hygiene system and method in which UVA light is delivered, by way of a specially adapted toothbrush or other device, directly to a photocatalyst deposited on the teeth, gums, tongue, and on other structures found in the mouth. The dental hygiene system and method, which delivers the UVA light from a source contiguous to the head of the toothbrush or other device, efficiently oxidizes and destroys potentially problematic bacteria or odorous compounds in the mouth. The potentially problematic bacteria and other organic species are associated with, for example, tooth decay, gum disease, denture stomatitis and halitosis/malodor. The dental hygiene system and method also whiten the teeth by oxidizing stains. This invention can also be used for the disinfection of dentures inside or outside of the mouth. Finally, as a part of the overall system and method, this dental hygiene system and method also disinfects key areas of the toothbrush or other device used to deliver the UVA light.

The use of photocatalysis in purifying both gas and liquid media and in controlling bacteria and other microorganisms on the surfaces of solid objects is a relatively new and rapidly growing technology. This photocatalysis process entails the illumination of catalytic n-type semiconductor particles (such as $TiO_2$ particles) with UVA light. It is believed that the UVA light promotes photoexcitation of valence band electrons and holes in the semiconductor particles, and that the electrons and holes migrate to the surface of the semiconductor particles to participate in reduction/oxidation reactions with matter adsorbed to or in the near vicinity of the surface of the particles. It is further believed that these reduction/oxidation reactions produce highly reactive hydroxyl radicals which oxidize and ultimately destroy certain organic species in the gas or liquid media, or on the semiconductor-bearing surfaces being treated.

The use of photocatalysis of certain organic compounds and dyes, and of catalytic n-type semiconductor particles in promoting dental hygiene is known to a limited extent. More particularly, U.S. Pat. No. 6,343,400 to Massholder describes a photocatalytic cleaning method for destroying bacteria on teeth and gums, whitening the teeth, and removing other organic impurities in the mouth. This method employs a toothbrush as a light guide to deliver UVA light to the mouth. The toothbrush includes a brush in its distal end in which at least some bristles are optical fibers. Just as in conventional toothbrushes, the bristles mechanically remove plaque from the teeth as they are brushed. As the brushing proceeds, the optical fiber bristles guide UVA light from the grip area at the proximal end of the instrument onto the tooth and gum surfaces where, together with a catalytic semiconductor, oxidative cleaning is produced by way of the photocatalysis process discussed above. As Massholder explains, the combination of mechanical cleaning with the UVA-light-induced oxidation increases the effectiveness of the brush, particularly with regard to the control of certain germs. Also, the bristles displace the semiconductor repeatedly from one point to another to further enhance the oxidation process.

Figure 1:
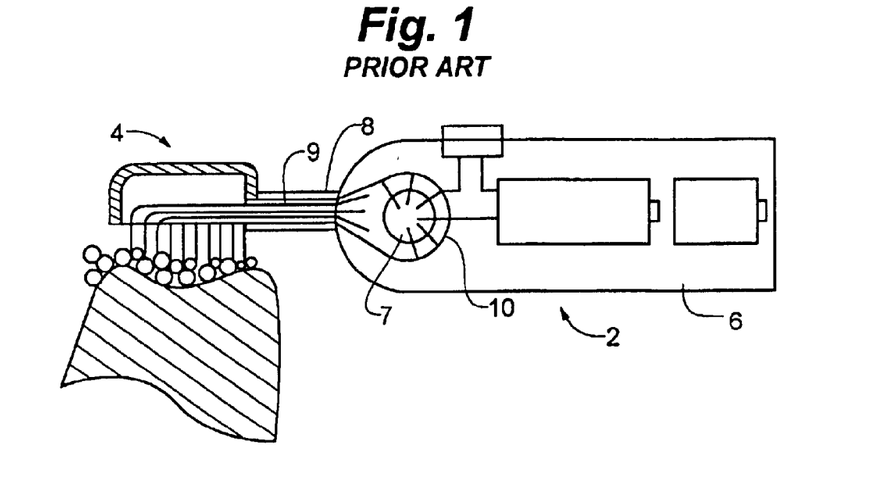
FIG. 1 illustrates the prior art device described in U.S. Pat. No. 6,343,400.

Massholder's prior art instrument for delivering UVA light to the mouth is illustrated in FIG. 1. This device comprises a toothbrush 4 at its distal end with a handle 6 containing a UVA light source 7 at its distal end. The UVA light source generates UVA light with a wavelength in the range of 320 to 400 nm. The UVA light is guided to the brush head 4 via a light guide 9 comprising a number of light-guiding fibers positioned in the stem 8 of the toothbrush. A reflector 10 is also provided to direct the UVA light into the entrance of the light guide 9.

Since the period of irradiation of the catalyst in any particular location in the mouth is very short during the toothbrushing process, and significant attenuation of the radiation strength occurs in its transmission within any optical fibers, it would be highly desirable to be able to provide a way of safely intensifying the effectively delivered UVA light by delivering the UVA light directly from the light source to the semi-conductor particles. This would eliminate the fall-off of the intensity of the initial UVA light by eliminating absorption in the fibers and hence accelerate the oxidation process, thereby maximizing the effectiveness of the overall system.

SUMMARY OF THE INVENTION

Our invention generally comprises a device for delivering UVA light directly to a photocatalyst deposited on the teeth, gums, tongue, and on other structures found in the mouth, from a UVA light source contiguous to the head of the device. The photocatalyst comprises catalytic n-type semiconductor particles, preferably $TiO_2$. The UVA light source is located contiguous to the head of the device which makes it possible to move the source of UVA light into close proximity to the location to which the UVA light is intended to be applied, the photocatalyst deposited on the teeth, gums, tongue, and on other structures found in the mouth. This delivery of the UVA light directly to the photocatalyst avoids the attenuation experienced when delivering UVA light indirectly such as by way of an optical fiber associated with a remote UVA light source.

The catalytic particles are applied to teeth, gums, and other oral surfaces, and photoexcited by UVA light supplied from the contiguous light source to oxidize and destroy potentially problematic organic species residing in the mouth. The UVA light source should be capable of producing UVA light with a wavelength in the range of about 350 nm to about 420 nm, and preferably at about 365 nm. At present, commercially available UVA producing LEDs are preferred light sources. Non-LED light sources as well as broader wavelength light sources that include the UVA spectrum in the absence of deleterious wavelengths may also be used.

In one embodiment, the inventive device is a toothbrush having tufts of bristles mounted to the top surface of the head of the toothbrush at its distal or working end. In this embodiment, placement of the UVA source may be near the center of the top surface of the head just below, just above, or at its surface and surrounded by the field of bristle tufts, just below, just above, or at the top surface of the head but outside of the field of tufts, at any edge of the head, or within the head directly below the proximal tips of the bristles, etc., as described in more detail below. In other embodiments, the device may be a tongue scraper, a flossing device, an interdental brush, a dental hand tool, a denture brush, or a UVA wand or probe. In these devices as well, the UVA light source will be positioned at or near the working end of the device to insure that the UVA light is delivered directly to the intended photocatalyst-coated oral surfaces.

The n-type semiconductor particles may be deposited on the oral surfaces in a variety of different ways. For example, when the device that is being used is a toothbrush, the n-type semiconductor particles can be incorporated into the dentifrice used with the toothbrush. Alternatively, the n-type semiconductor particles may be deposited by incorporating them in a mouthwash or rinse, by putting them into a gel applied directly to the surfaces to be treated, or by putting them in the water stream delivered by a dental hand tool.

BRIEF DESCRIPTION OF THE FIGURES

The features of this invention which are believed to be novel are set forth with particularity in the appended claims. The invention, together with its objects and advantages, may be best understood by reference to the following description taken in conjunction with the accompanying drawings, in which like reference numerals identify like elements in the several figures and in which:

DETAILED DESCRIPTION OF THE INVENTION

Figure 2:
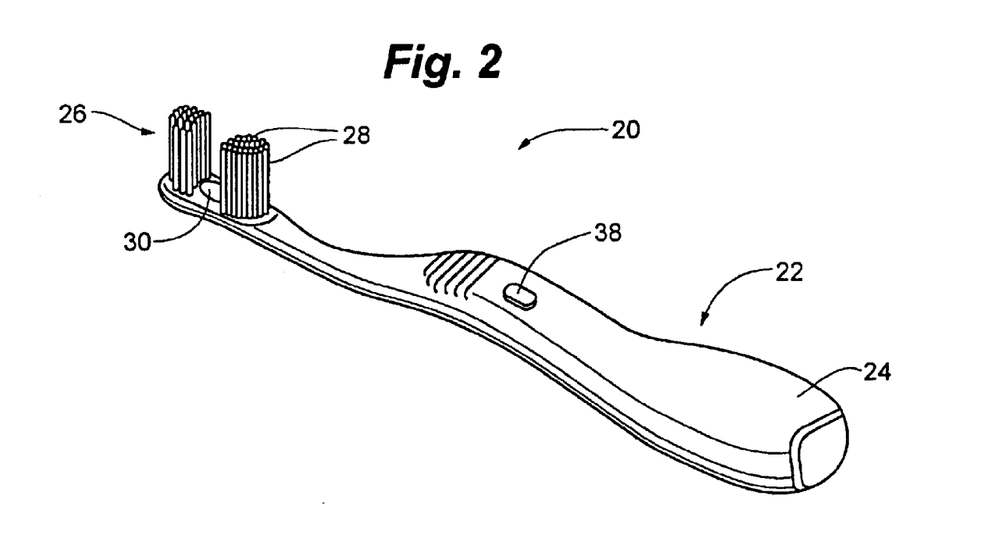
FIG. 2 is a perspective view of a toothbrush in accordance with the present invention, having a UVA light source mounted near the center of the top surface of the toothbrush head, surrounded by tufts of bristles.
Figure 3:
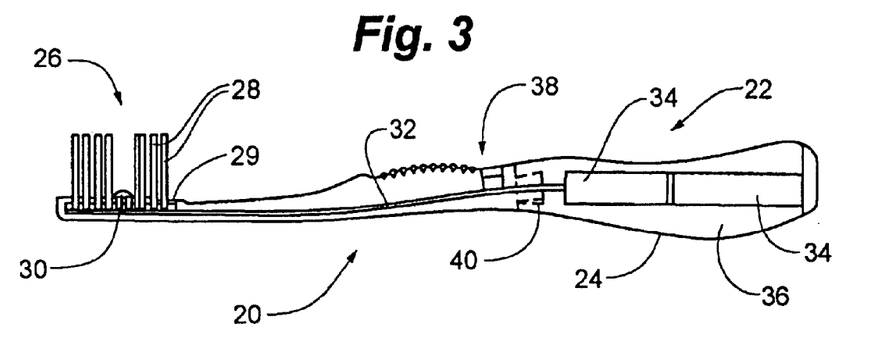
FIG. 3 is a side elevation view of the toothbrush of FIG. 2.

Turning now to FIGS. 2 and 3, a toothbrush 20 in accordance with the present invention is illustrated. Toothbrush 20 includes a handle 22 with a grip 24 at its proximal end to be held in the user's hand when using the toothbrush. A toothbrush head 26 having a grouping of conventional tufts 28 of bristles mounted in its top surface 29 is located at the distal or working end of the toothbrush. A UVA light source 30 is provided contiguous to the head at the top surface of the toothbrush head to radiate UVA light into the area of the mouth (particularly teeth, gums, and tongue) being contacted by the bristles of the toothbrush head as it is used in brushing the teeth.

Figure 21:
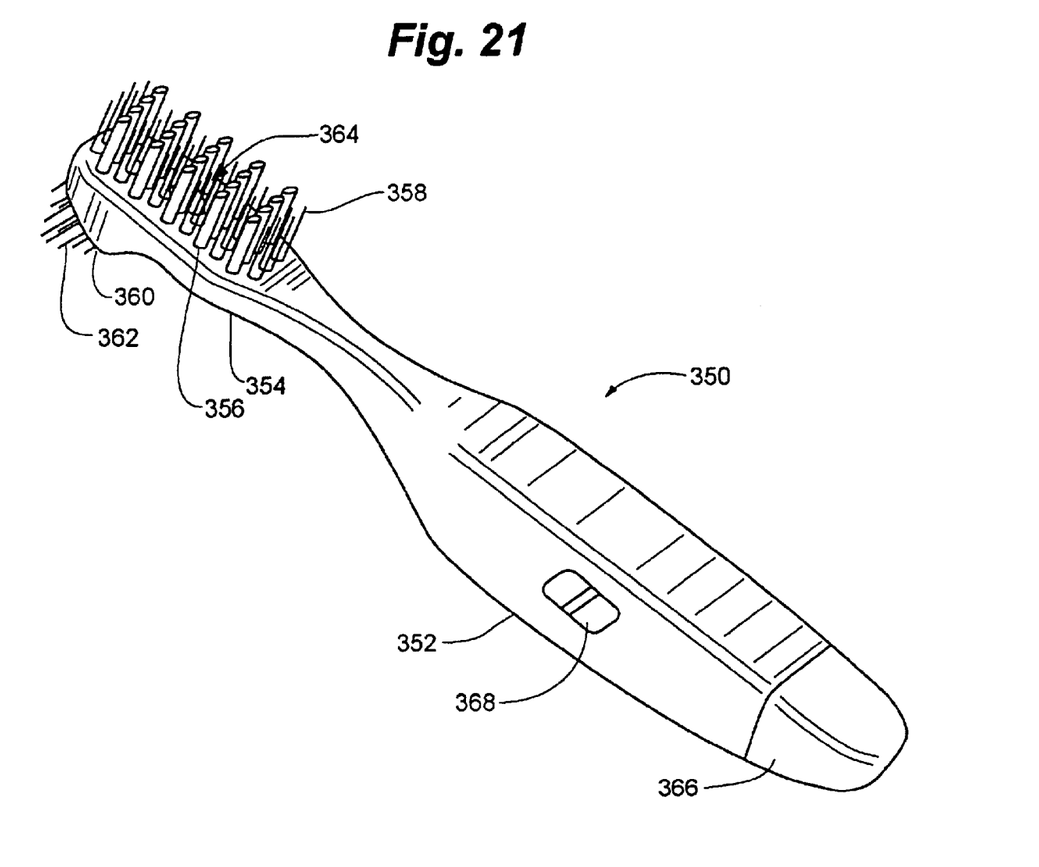
FIG. 21 is a denture brush in accordance with the present invention, having a UVA light source mounted near the center of the toothbrush head, surrounded by tufts of bristles.

While toothbrush 20 may also be used for cleaning dentures, whether in the mouth or outside of the mouth, a specially adapted denture brush is illustrated in FIG. 21, which is described below.

Figure 4:
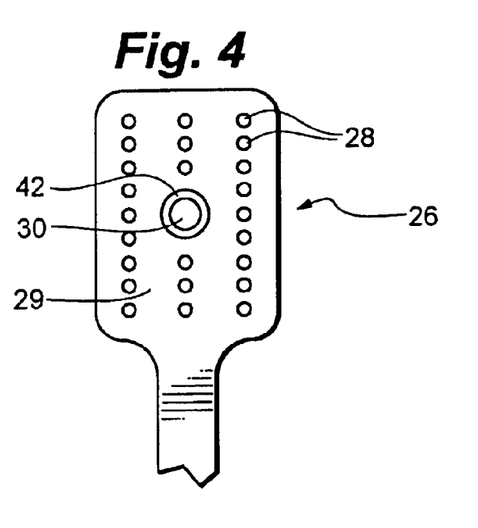
FIG. 4 is an enlarged partial top plan view of the head or working portion of the toothbrush of FIGS. 2, 3, and 3B.

In the particular embodiment of the invention of FIGS. 2 and 3, the UVA light source located contiguous to the head of the device is positioned generally in the center of the top surface of the toothbrush head (see FIG. 4). However, as will be seen from the discussion of alternate embodiments of the invention described below, the term "contiguous" is intended here to be understood as encompassing both of its conventional dictionary meanings of "in physical contact with" or "near, next to, or adjacent". A UVA light source that is not "contiguous" to the toothbrush head is one which is at a location that is not in physical contact with or near, next to, or adjacent the head, and that requires an optical fiber or other means to carry UVA light produced at a remote location to the head.

In the embodiment of the invention of FIG. 3C, the UVA light source 30 is located in the handle in a position just below the neck 15 of the device allowing the UVA light to enter the neck of the brush 16 in a direction towards the distal end of the head. This represents an alternative embodiment of the invention in which the light source is not contiguous to the head, but rather is continguous to the neck of the toothbrush handle. The UVA light entering the head is scattered in all directions including towards the face of the head to exit the head parallel to the tufts of bristles. This is shown in detail in FIG. 3D, where the portion of the neck in which the UVA light is transmitted 11 is made of a suitable transparent material and the back of the head 13 is applied as an over-mold or by another appropriate method so the interface of the two materials at facets 18 forms a reflective surface to redirect UVA light 21 from a path along and co-linear with the brush neck 15 to a direction 17 generally parallel to the bristles. In addition, other scattering of the UVA light in other directions (such as through the neck and the distal end of the head) would provide activity in other areas of the mouth.

Electric current is supplied to the UVA light source of toothbrush 20 by way of a pair of electrical conductors 32 connected to a battery of dry cells 34 located in a cavity 36 in the grip 24 at the proximal end of the handle. An energy cell, or wall current, or other power source could be used in place of batteries 34. A switch 38 is positioned in the circuit between the batteries and the UVA light source to interrupt current flow when the brush is not in use, and to supply current to the UVA light source when the brush is used. Also, recent advances in dry cell technology permit the mounting of the power source in the head immediately adjacent to the UVA light source. This could also include an integrated circuit in or near the head to detect use of the device in the mouth, and to control a timer to turn off the light source.

A timer may be provided to limit the period of illumination each time power is supplied to the LED. Such an optional timer 40, which can be supplied from myriad currently available mechanical and electronic designs, is represented in FIG. 3 as a broken line block. In yet another approach to turning the UVA light source on and off, a sensor could be placed in the toothbrush head to close the circuit and turn on the UVA light source when the toothbrush head is placed in the mouth by measuring conductivity, temperature, ambient light, or another parameter indicating that the toothbrush head is in the mouth. Alternatively, the handle may be provided with means for sensing the warmth or pressure of the user's hand to activate the device.

Figure 10:
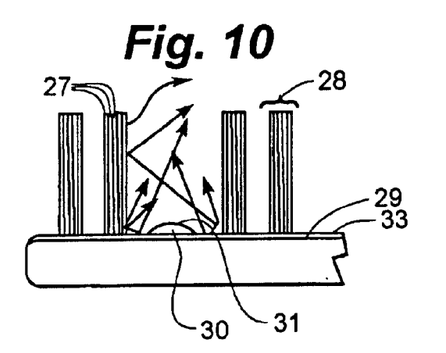
FIG. 10 is a side elevation view of a toothbrush head diagrammatically illustrating UVA light scattering off of reflective bristle surfaces.

While, as already noted, it is key to the present invention that the UVA light source be located in the head of the toothbrush (except in the alternate embodiment of FIGS. 3C and 3D), it is also useful for the UVA light produced by the light source to be distributed by reflection off the surfaces of the head and the bristles of the tufts surrounding or adjacent to the UVA light source. This will help distribute the UVA light into otherwise inaccessible regions, and sanitize the bristles and the surface of the toothbrush head, reducing bacterial growth on the head and the bristles of the toothbrush vis-à-vis that found in a conventional toothbrush after use. Furthermore, as illustrated in FIG. 10, some or all of the bristles 27 of tufts of bristles 28 and the surface 29 of the head may be coated with a metallic or other material 33 reflective to UVA light to further enhance the distribution and to maximize the availability of the UVA light delivered to the teeth, gums, and tongue. These reflective surfaces will direct the UVA light at glancing angle reflections to maximize the availability of the light interproximally and subgingivally along the bristles. Thus, light emitted by LED 30 may be directed at and scattered off the coated bristle sides 31 to be directed at surface 29 as shown, whereby the reflective surface 33 will redirect the light towards the working ends of the bristles where they contact the teeth.

Figure 3A:
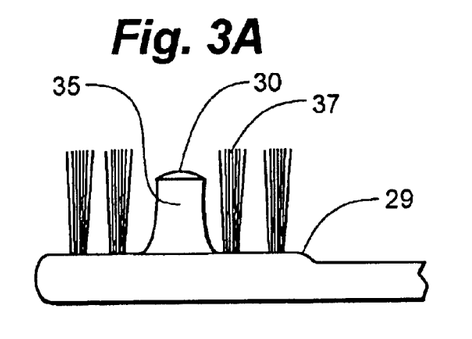
FIG. 3A is a side elevation view of an alternative embodiment of the toothbrush of FIG. 2 in which the UVA light source is mounted at the top of a column to bring the light closer to the functioning tips of the toothbrush bristles.

In another embodiment shown in FIG. 3A, the UVA light source 30 is mounted in a column 35 on the face of the brush head 29 to raise the source of the light closer to the functioning tips 37 of the bristles to concentrate the light energy at the needed location of action.

Figure 3B:
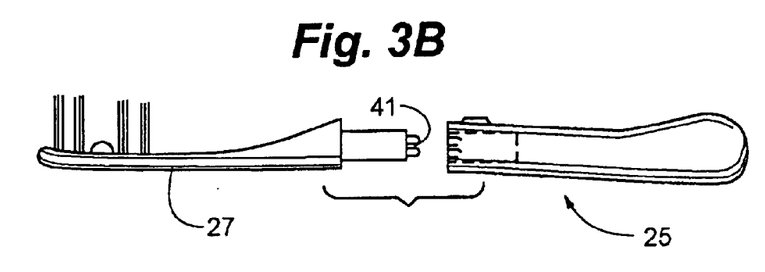
FIG. 3B is a side elevation view of an alternative embodiment of the toothbrush of FIG. 2 in which the toothbrush comprises a handle and a removable toothbrush head.
Figure 3C:
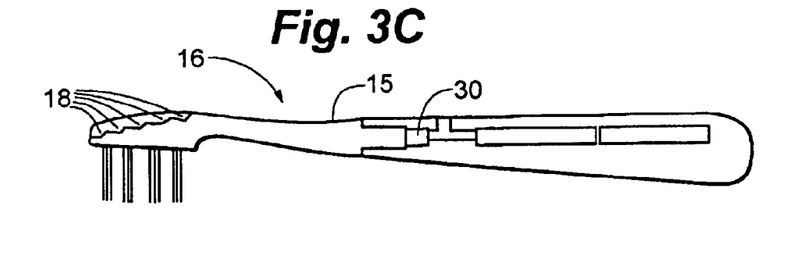
FIG. 3C is a cutaway side elevation view of an alternative embodiment of the toothbrush of FIG. 2 in which the UVA light source is located just below the neck of the device.
Figure 3D:
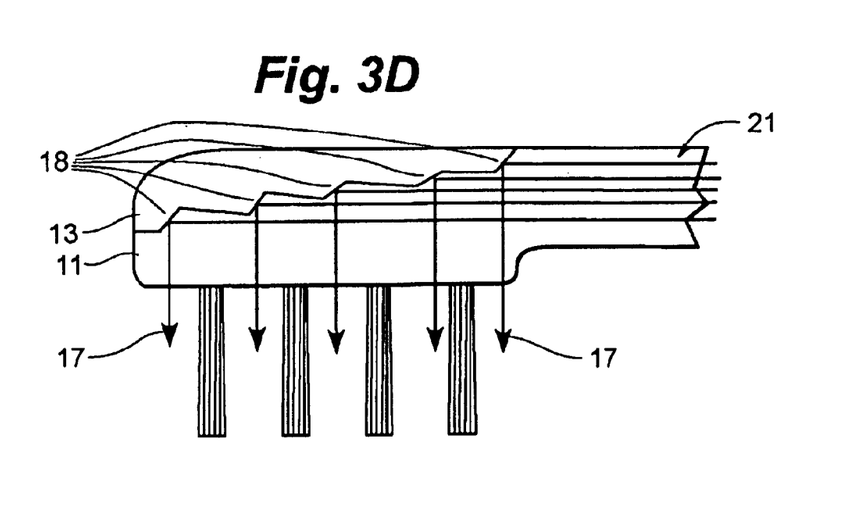
FIG. 3D is an enlarged view of the head of the device of FIG. 3C.

In a variation of the design of FIGS. 2–3, shown in FIG. 3B, the toothbrush may be provided with a replaceable head 27 removably attached to a handle 25. Appropriate mating electrical contacts 41 will be provided in the head and the handle to insure proper electrical continuity when the removable head is mounted to the handle. This would make it possible to replace the head when either the bristles or the UVA light source is spent. It would also make it possible to use a single handle with a variety of different sizes and types of heads. Indeed, just as a handle with a power supply can accept a replaceable toothbrush head to generate UVA light for delivery to the teeth and mouth, so might the handle accept other devices as replaceable heads such as a tongue scraper, an interdental brush, a flosser, or a wand.

Turning now to FIG. 4, the embodiment of toothbrush head 26 of FIGS. 2 and 3 is shown in enlarged form, in a top plan view. The head in this embodiment includes a field of conventional bristle tufts 28, mounted by conventional metal anchors or hot melt insertion, arranged in a desirable pattern generally across the top surface of the head.

The single LED 30 capable of producing UVA light in the range of about 350 nm to about 420 nm, and preferably at about 365 nm is mounted at the center of the head, optionally protruding therefrom, so that it can provide UVA light to the teeth, gums, and tongue when activated by turning on a switch or by other means as discussed above. The proximity of the UVA light source to the location at which the UVA light is to be supplied, free of the attenuation experienced when delivering the UVA indirectly through an optical fiber, is an important advantage of this invention. A second important advantage is the light reflection and scattering from the bristle surfaces, providing beneficial photocatalytic tissue crosslinking and oxidative effects in areas where bristle tips do not enter. In order to prevent migration of fluid into the interior of the head, LED 30 may be potted in place with plastic 42, epoxy, or other water resistant potting material, with an appropriately sized gasket, or with other sealing means. LED 30 has two leads on its bottom (not shown) which are electrically connected to conductors 32 (FIGS. 2 and 3).

Figure 5:
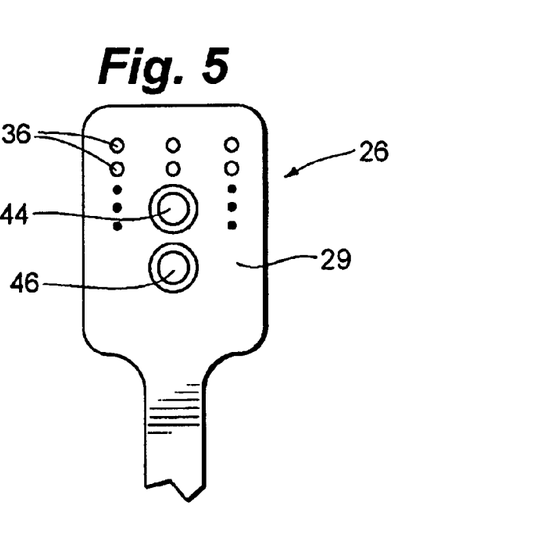
FIG. 5 is another enlarged partial top plan view of the head portion of a toothbrush in accordance with the present invention, having two UVA light producing LEDs mounted in the head, surrounded by a field of tufts of bristles.

Turning now to FIG. 5, another embodiment of toothbrush head 26 is shown in enlarged form, in a top plan view. In this embodiment, head 26 includes a field of conventional bristle tufts 28 located generally across the head as in FIG. 4. Two LEDs 44 and 46 capable of producing UVA light in the desired wavelength range described above are mounted along the central longitudinal axis of the head so that they can supply UVA light to the teeth and gums when activated by turning on switch 38. The LEDs are surrounded by the field of bristle tufts.

Figure 6:
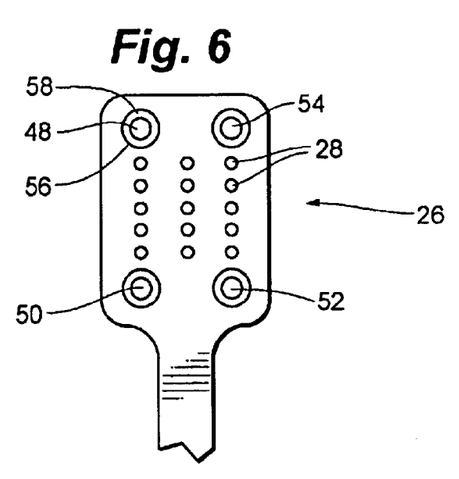
FIG. 6 is another enlarged partial top plan view of the head portion of a toothbrush in accordance with the present invention, having four UVA light producing LEDs located at the four corners of the head, outside of the field of tufts of bristles.

Yet another embodiment of toothbrush head 26 is shown in FIG. 6 in enlarged form, in a top plan view. The head, which is generally rectangular, includes a field of conventional bristle tufts 36 located across the head as in FIGS. 4 and 5. Four LEDs, 48, 50, 52, and 54 capable of producing UVA light in the earlier noted wavelength range are mounted at the corners of the head beyond the field of tufts of bristles to supply UVA light to the teeth, gums, and tongue when activated 38. These LEDs are sealed in place in circular cavities 56 by rubber "O" rings 58.

Figure 7A:
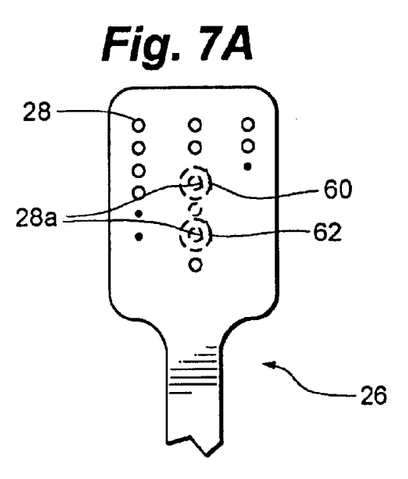
FIG. 7A is an enlarged partial top plan view of the head portion of a toothbrush in accordance with the present invention, in which UVA light producing LEDs are mounted directly under the bristle tufts of the toothbrush
Figure 7B:
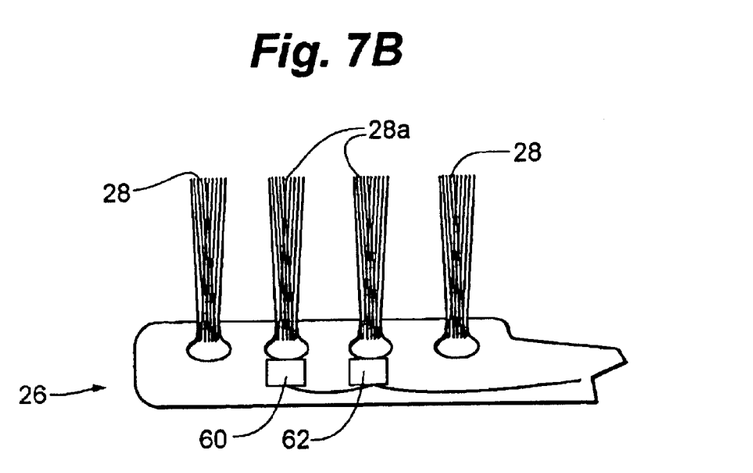
FIG. 7B is cutaway side view thereof.

Turning next to FIGS. 7A and 7B, a further embodiment of toothbrush head 26 is shown in enlarged form, in a top plan and a section view respectively. Head 26 includes a field of conventional bristle tufts 28 located generally across the head. Two LEDs, 60 and 62, capable of producing UVA light in the desired wavelength range are mounted in the toothbrush head directly under bristle tufts 28a to supply UVA light to the teeth, gums, and tongue through and past spaces between the bristles of the tufts when activated. In one desirable embodiment, the bristles will be mounted in the head of the toothbrush by hot melt insertion so that the inserted ends of the bristles of each of the tufts are melted into a generally unitary ball and pressed near or against the LED to maximize UVA transmission through as well as along the bristles. In this embodiment, the bristles should be capable of transmitting UVA light. Also, it is noted that placement of the UVA light source in the head insures substantially better UVA light delivery due to the short distance for light transmission than that produced over an optical fiber with a UVA light source at a remote location. That prior approach suffers from attenuation over the length of the fiber and the difficulties of bending the UVA light around corners to direct the UVA light upwardly through the head of the toothbrush.

Figure 8:
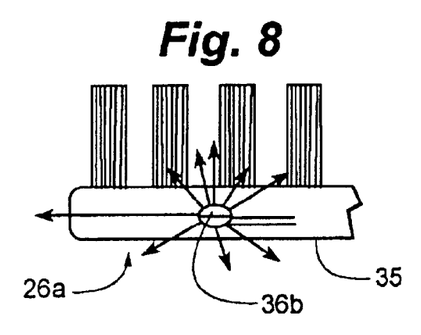
FIG. 8 is an enlarged partial plan view of the head portion of a toothbrush in accordance with the present invention in which the head is made of a material which passes UVA light from a UVA light source located within the head.

In FIG. 8, a toothbrush head 26a is made from a material which readily passes UVA light such as polyester. UVA light-producing LED 36b is mounted within the head so that the UVA light is emitted from the front, back, and sides of the head. Various portions of the surface of the head may be rendered non-UVA-transmitting by coating those surfaces with a material that blocks UVA light. For example, the back surface 35 of the head may be coated with such a UVA blocking material. If such a UVA-blocking coating is applied, it is preferred that it also be reflective to UVA light to reflect the UVA light produced by LED 36b from the desired portions of the head to exit at the uncoated areas.

Figure 9:
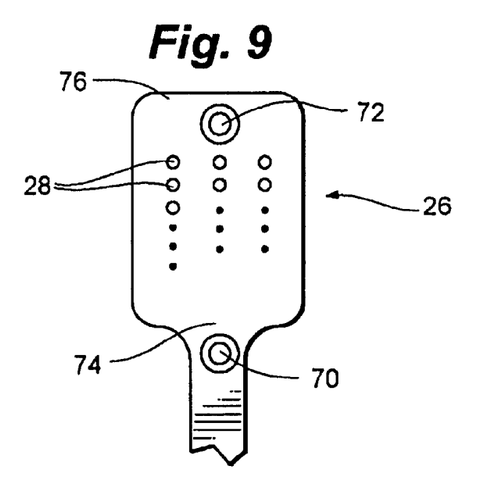
FIG. 9 is an enlarged partial top plan view of the head portion of a toothbrush in accordance with the present invention in which UVA light producing LEDs are mounted beyond the field of tufts of bristles at the distal and proximal ends of the head.

In FIG. 9, another embodiment of toothbrush head 26 is shown in enlarged form, in a top plan view. In this embodiment, head 26 includes a field of conventional bristle tufts 28 located generally across the head. Two LEDs, 70 and 72, capable of producing UVA light in the desired wavelength range are mounted respectively beyond the field of tufts of bristles below the proximal end of the head 74 and at its distal end 76 to supply UVA light to the teeth, gums, and tongue when activated.

Figure 11:
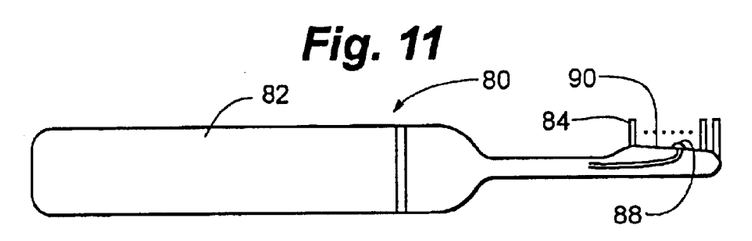
FIG. 11 is a side elevation view of a power toothbrush in accordance with the present invention, in which a UVA light source is located near the center of the top surface of the toothbrush head.

The direct UVA lighting described in connection with the manual toothbrushes of FIGS. 2–9 above could also be implemented using powered toothbrushes which, inter alia, move the tufts in a stroking motion, in a circular motion, or in a vibratory motion, as illustrated generally in FIG. 11 by powered toothbrush 80. Toothbrush 80 includes a gripping portion 82 at its proximal end in which a battery (not shown) is held. These batteries power a motor (not shown) that moves the toothbrush tufts of bristles 84 mounted in the head 86 of the device in the desired stroking motion, circular motion, or vibratory motion. Toothbrush 80 also includes one or more UVA light sources 88 mounted near the center of top surface 90 of toothbrush head 86. Light source 88 is powered by the batteries that power the motor of the device and may be turned on and off with the motor, or separately, as desired. The motion produced by a powered toothbrush moves about and mixes the photocatalyst, improving the distribution of the photocatalyst and therefore enhancing its activity. Powered toothbrush 80 may, of course, be provided with a replaceable, removably attached head, as described earlier in connection with the manual toothbrush of FIG. 3B.

Figure 12A:
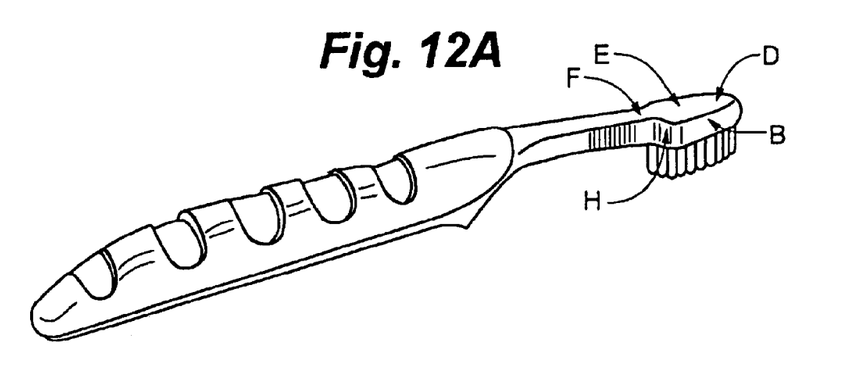
FIGS. 12A–12C depict a toothbrush handle in accordance with the present invention, in perspective (FIGS. 12A and 12C), and top plan (FIG. 12B) views in which additional sites contiguous to the toothbrush head at which UVA light sources could be located in accordance with the present invention are highlighted.
Figure 12B:
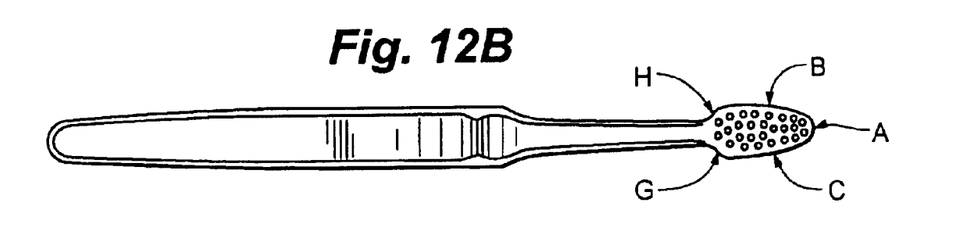
Figure 12C:
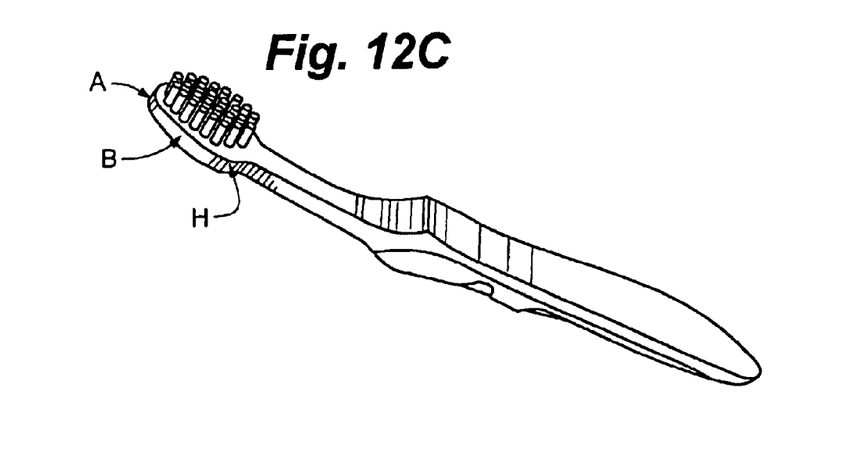

As noted above, an important aspect of the present invention is to position the UVA light source contiguous to the head to produce direct UVA excitation near the head, thereby avoiding or minimizing the losses in UVA intensity and other difficulties inherent in carrying UVA light to the head from a remote source, over optical fibers, or otherwise. Contiguous placement of the UVA light source and numbers of light sources other than those illustrated in FIGS. 2–11 may be used. These placements can be at or near any one or more of sites A-H in FIGS. 12A–12C.

Figure 13:
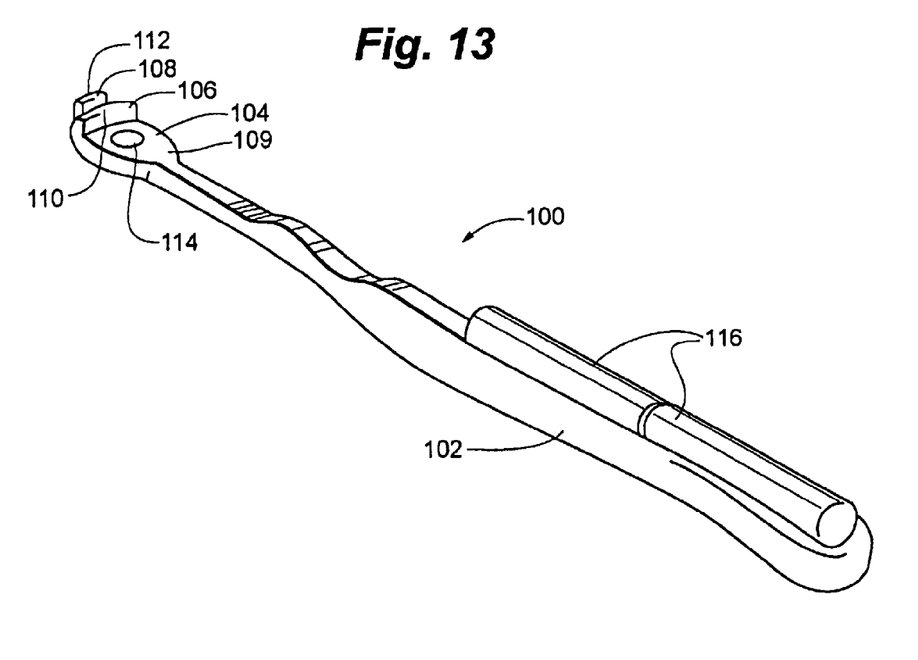
FIG. 13 is a perspective view of a tongue scraper in accordance with the present invention, in which an LED is located in the head of the device, proximal to the scraping surfaces of the device.

FIG. 13 illustrates, in perspective view, an alternative type of device in accordance with the invention. The device of FIG. 13 is a tongue scraper 100 including a handle 102 at its proximal end, and a scraper head 104 at its distal end. Scraper head 104 includes two upstanding slightly arched lips 106 and 108 having respective arcuate top edges 110 and 112. An LED 114 capable of producing UVA light is potted into head 104 preferably near its center, just below the top surface 109 of the head, and in close proximity to lip 106. Batteries 116 in the handle of the device provide current to the LED by way of a pair of wires (not shown) in the handle. The handle also includes a switch (not shown) much like that described in the toothbrushes referred to above, to turn the LED on and off.

The patient uses the tongue scraper as follows. First, the patient grasps the handle and turns on the switch. Then, the handle is inverted from the disposition shown in FIG. 13 so that the upstanding lips 106 and 108 are oriented downwardly with respect to the top of the user's tongue. The device is then repeatedly inserted into the patient's mouth as far back as comfortable, pressed down onto the tongue, and pulled forward to both scrape the tongue's surface and subject it to the UVA light produced by the LED in the head of the device. The device may, of course, be manipulated within the mouth to also scrape the sides and bottom of the tongue, if desired. Also, the scraper head may be designed as a separate part for removable attachment to a handle interchangeable with a removable toothbrush head as described above in connection with FIG. 3A.

Use of this device does not require that a photocatalyst be applied to the tongue or the device. But this—if used—may be in the form of a gel or other material containing photocatalyst which is applied to the tongue before the scraper is used. Alternatively, a dentifrice containing the photocatalyst may be used by either applying dentifrice directly to the tongue, or by brushing the teeth with the dentifrice and, before rinsing the dentifrice from the mouth, turning to the use of the scraper to scrape the tongue and to activate photocatalyst already deposited on the tongue or on the device. It is anticipated this type of device will also find use in the surface cleaning and photocatalytic disinfection and crosslinking of articular surfaces such as those in temporomandibular joints or knee and other joints outside of the mouth that are accessed via arthroscopic surgery.

Figure 14:
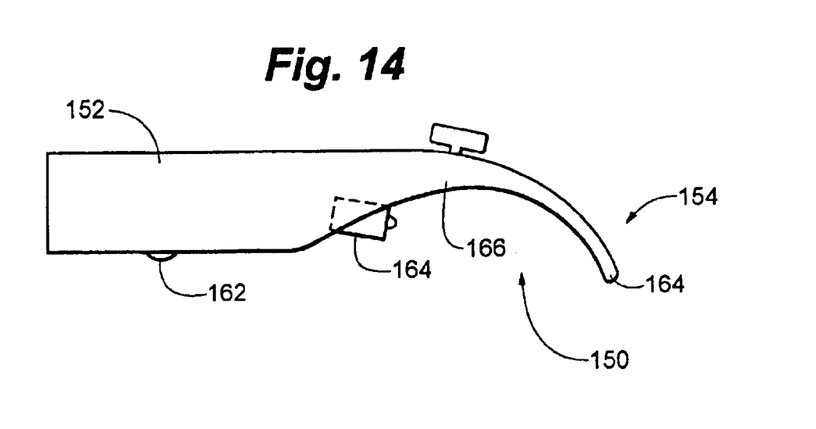
FIGS. 14 and 15 are respectively side and top views of a flossing device in accordance with the present invention, in which a UVA light source is located at a strategic location vis-à-vis the floss mounted in the head of the device.
Figure 15:
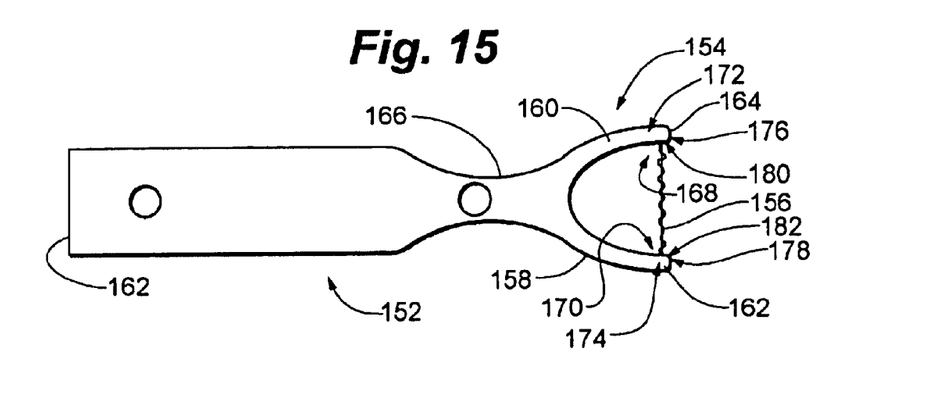

FIGS. 14 and 15 illustrates a flossing device in accordance with the present invention. This device 150 includes a gripping portion 152 at its proximal end, and a flossing head 154 at its distal or working end. A length of floss 156 is fixed in the head by attachment to ends 162 and 164 of arms 158 and 160 of the device. The floss may be permanently attached (as shown) or it may be disposably mounted in the ends of the arms by conventional means, to be advanced and discarded as it is used. This device has a power source (not shown) in its gripping portion 152 and a pushbutton switch 162 to turn the UVA light source on and off.

A UVA light source 164 may be positioned as shown just below the neck 166 of the flosser protruding slightly from its surface. In addition, or alternatively, UVA light sources may be positioned on the inside of arms 158 and 160, below the point of attachment of the floss, at points 168 and 170. In yet another embodiment, alternating UVA light sources may be provided on the bottom surfaces 172 or top surfaces 174 of the arms or at their tips 176 and 178. Finally, UVA light sources may be positioned within the arms, adjacent the ends of the floss, at points 180 and 182, to direct UVA light along the floss positioned between the ends of the arms. In this embodiment, the arms and the floss are preferably made of materials that conduct UVA light. Each of the placements described above will, of course, produce UVA light from locations contiguous to the head of the device to produce activation in different locations within the mouth while the flossing device is used.

Figure 16:
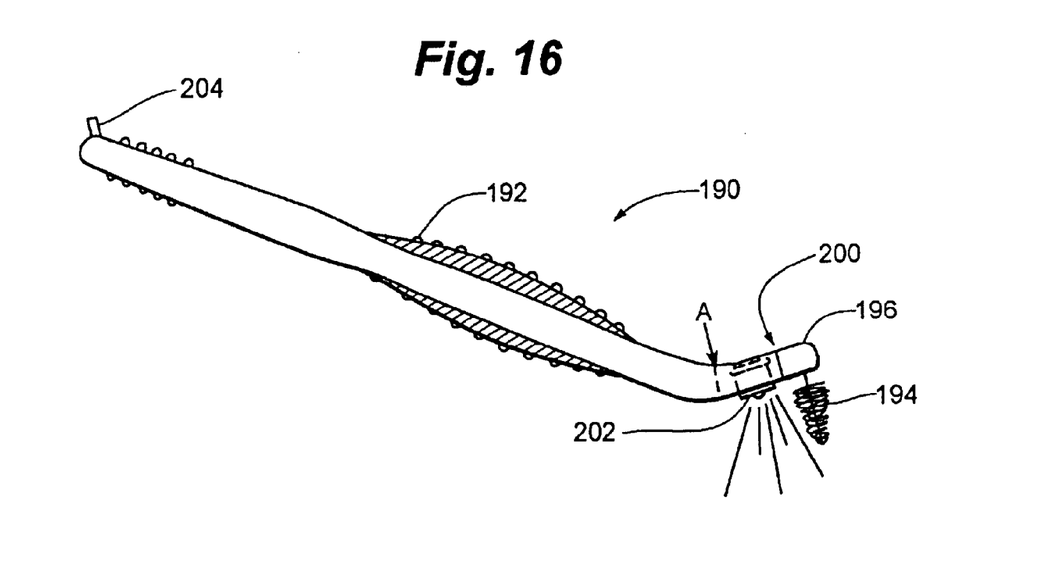
FIG. 16 is a perspective view of an interdental brush handle in accordance with the present invention, in which a UVA light source is located below the interdental brush in the head of the device.

FIG. 16 illustrates yet another embodiment of the invention, an interdental cleaning device 190 including a handle gripping portion 192 at its proximal end and an interdental brush 194 in the distal or working end of the device. This interdental cleaning device may have a replaceable or interchangeable brush member 196 carrying brush 194 which can be removed from the device by separating it at separation line 200. Alternatively, the device may be designed for replacement of individual brushes 194. Various approaches to mounting and replacing brushes are illustrated in U.S. Pat. Nos. 4,691,404; 4,710,996; 4,805,252; and 5,347,675 to John O. Butler Company.

Interdental cleaning device 190 includes a UVA light source 202 positioned contiguously to the working end of the device. This light source is connected to a power source in the proximal end of the device by wires within the gripping portion running from the light source to the power source (not shown). A switch 204 is also provided to turn the light source on and off. Finally, it is noted that the light source may be located in the interchangeable brush member 196, effectively moving separation line to position A in the figure. In such an embodiment, mating electrical contacts would be provided in the base of the interchangeable brush member and in the corresponding end of gripping portion 192 of the device.

Figure 17:
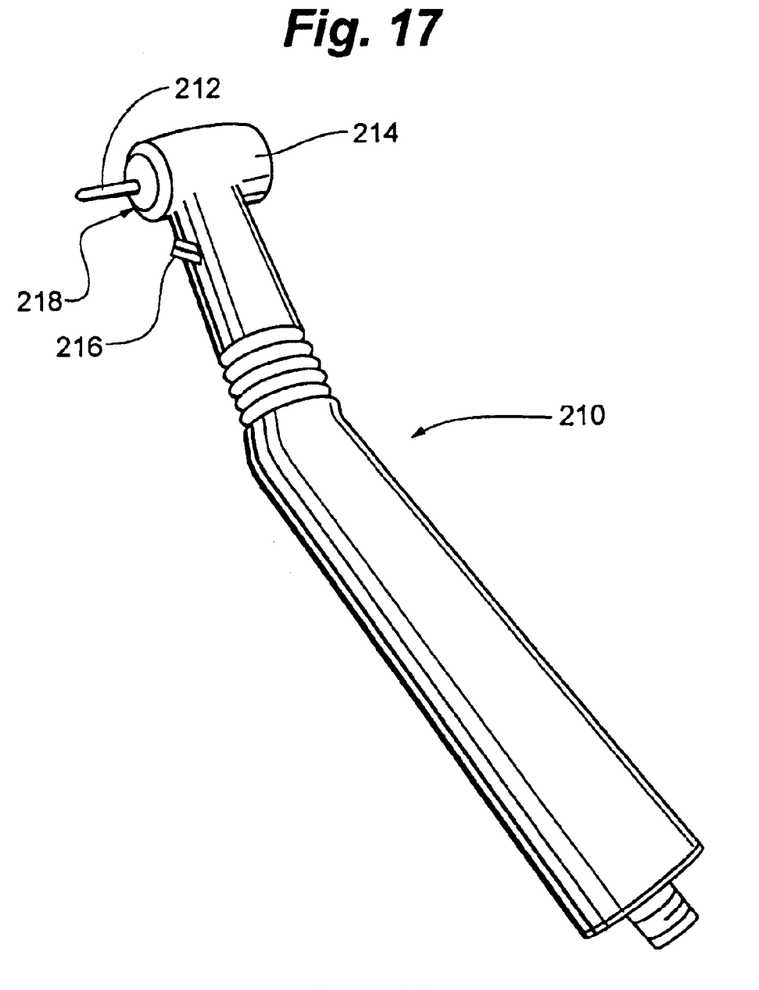
FIG. 17 is a perspective view of a dental handpiece in accordance with the present invention, in which a UVA light source is located just proximally to the bur mounted in the handpiece.

A dental handpiece 210 is shown in FIG. 17 with a cutting bur 212 mounted in the distal end of the device. The bur is driven by a conventional mechanism mounted in the head 214 at the distal end of the device which, in turn, is supplied with power from a source connected at the proximal end of the handpiece (not shown). A UVA light source 216 powered by the handpiece is mounted contiguously to head 214 at the distal end of the device so that UVA light can be applied about the area contiguous to the bur as the handpiece is employed in e.g., drilling or other dental operations. Additionally, fluid (typically water) sprays from the handpiece through ports 218 as the bur is operated to cool the bur as it operates. In one embodiment of the invention, this fluid will include a photocatalytic dye and/or n-type semiconductor particles which will coat the surfaces subject to the UVA light. In other embodiments, photocatalyst and/or inorganic the n-type semiconductor particles may be applied as a rinse, a paste, or by other practical means.

Figure 18:
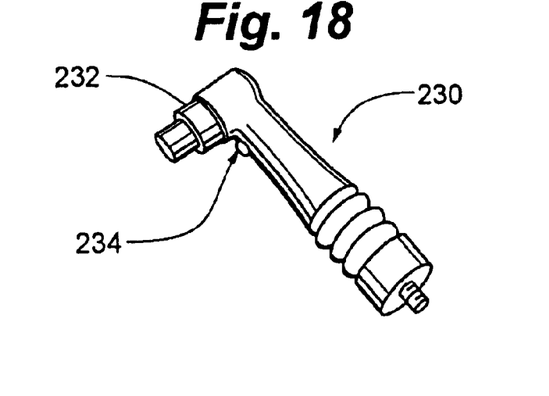
FIG. 18 is a perspective view of a disposable prophy angle in accordance with the present invention, in which a UVA light source is located just proximally to the flexible polishing cup.

FIG. 18 shows a disposable prophy angle 230 with a flexible cup 232 which is used to polish the teeth with prophy paste. Prophy angle 230 is supplied with a UVA light source 234 located contiguously to the flexible cup to shine UVA light on the teeth and the prophy paste during prophylaxis. This prophy paste will include n-type semiconductor particles or other photocatalytic reagents which will be photoactivated by the UVA light.

A device may also be provided in accordance with the invention which is specifically and exclusively intended to be used for purposes of supplying UVA light. Such a device is illustrated by the UVA wand 300 of FIGS. 19 and 20. This device includes a power source 302, with a rheostat 304 and an on/off switch 306. A flexible conduit 308 is attached to the power source and carries current through a pair of wires in its interior to a head 310 at the distal end of the conduit. Head 310 has a UVA light source 312 at its tip (considered "contiguous to the tip" for purposes of this invention) for directing UVA light along the longitudinal axis of the head. The UVA light source is turned on and off by switch 306. The power supplied to the UVA light source and hence its intensity may be adjusted by operating rheostat 304. In the alternate embodiment illustrated in FIG. 20, the UVA light source is mounted in head 310A at a generally 90° angle to the longitudinal axis of the head.

Figure 19:
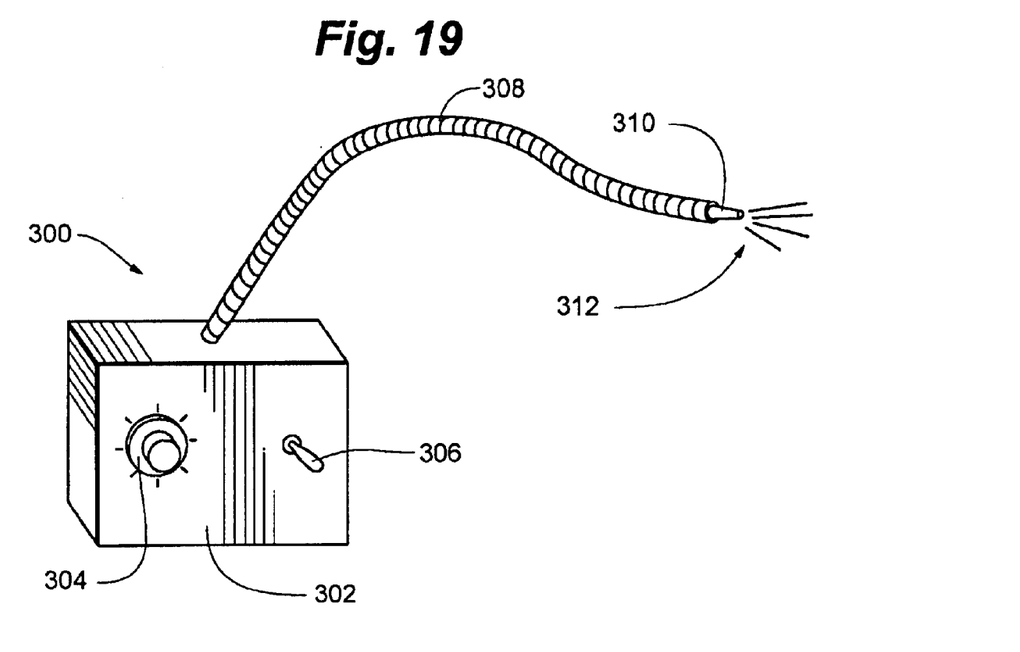
FIGS. 19 and 20 are perspective views of two versions of a wand or probe with a UVA light source at its proximal end for directing UVA light to desired locations in the mouth.
Figure 20:
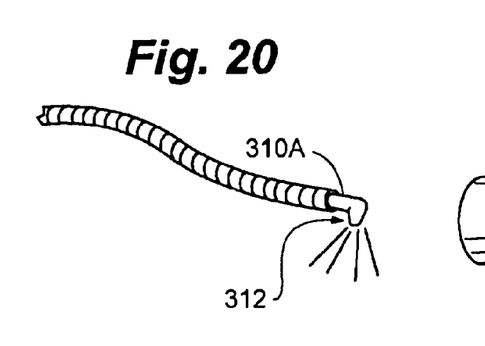
Figure 20A:
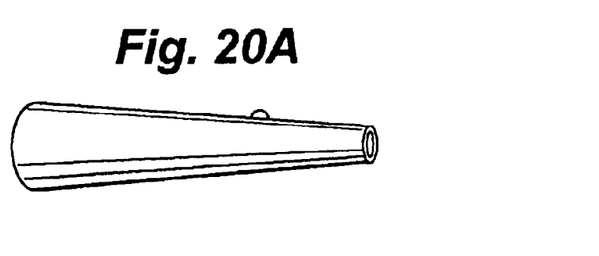
FIGS. 20A, 20B, and 20C are alternative wand designs.
Figure 20B:
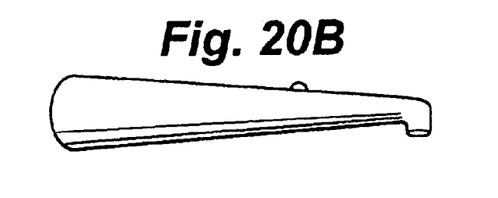
Figure 20C:
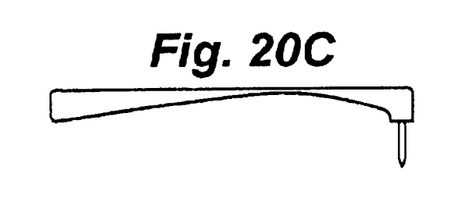

The wand or probe of FIGS. 19 and 20 is designed be inserted in the mouth or into any other body opening or orifice after photocatalyst is applied, and moved about to activate the photocatalyst where desired. It would be most likely to be used by an oral care professional who can observe the UVA light source as it is moved to the desired locations within the mouth, and who will be skilled in determining how long to expose particular photocatalyst-coated areas. While the unit described above is anticipated to be a wall-powered unit, a battery powered unit configured as shown in FIG. 20a or 20b may be used by the professional as well. It may be a probe for delivery of the desired UVA light to small, difficult-to-access locations between teeth or under the gum line by a device as shown in FIG. 20c. Also, the wand or probe could also be used by oral/maxillofacial surgeons and orthopaedic surgeons while performing arthroscopic repairs to articulating joints.

In the final figure illustrating an embodiment of the present invention, a denture brush 350 is shown. The brush includes a gripping area 352 at its proximal end, and a head area 354 at its distal or working end. The head of the denture brush includes on one of its faces 356 a field of tufts of bristles 358 projecting outwardly from the face. The denture brush also includes projecting from a plane 360 that intersects the plane of face 356 at an acute angle a series of particularly stiff bristles 362 that project down and away from the distal end of the denture brush. A UVA light source 364 is located contiguous to the head area of the device, positioned generally in the center of the top surface of the denture brush head. A second UVA light source is positioned in the center of the acute angled plane (not shown). A power source in the form of a power cell (not shown) is mounted in the proximal end of the handle to supply a current to the UVA light sources, and a cap 366 is provided at the proximal end of the handle to access the power cell when necessary. Finally, a three-position switch 368 is provided to choose between the off position and the on position for either one of the two UVA light sources.

This brush is not primarily intended for use in the mouth. Rather, it is intended to be used in cleaning dentures that are removed from the mouth. These dentures are first soaked in a photocatalyst-containing solution to ensure that photocatalytic molecules or particles are distributed on the surfaces of the teeth in the denture being cleaned. As either of the brushes are used to clean the dentures, activation of the photocatalytic dye and/or $TiO_2$ particles coated on the teeth helps destroy deleterious bacteria present on the denture surfaces and can also provide a whitening effect. Additionally, the denture brush head may be dipped into a photocatalyst- or $TiO_2$-containing solution periodically during the cleaning process to apply organic catalyst or inorganic $TiO_2$ particles from the solution to the teeth surfaces and activate those materials in a near simultaneous process.

It is presently believed that the commercially available UVA producing LEDs that could be used in the invention are available from: Nichia America (e.g., NSHU 550-gallium indium nitride UV) and Cree CXXX-MB290-EXXXX series LEDs. Also, insofar as electrically powered UVA sources mountable in the head other than LEDs are available, alternative UVA sources could be used in the present invention. For example, a Homamatsu Lightningcure LC5 series 200W mercury-xenon bulb could be used. Other examples include micro-fluorescent bulbs and micro-incandescent bulbs which include UVA spectrum in the absence of deleterious light wavelengths. Also, customcrafted gas plasma discharge UVA bulbs could be used.

Finally, it appears that it may be possible to render $TiO_2$ (and possibly other catalytic n-type semiconductor particles) as responsive to visible light as some of the photocatalytic organic dyes already known in the art. Such a product comprising $TiO_2$ coated with apatite is believed to be currently available from a Japanese firm known as Ecodevice. Insofar as catalytic semiconductor particles responsive to visible light become available, the UVA light source in the above embodiments of this invention may be replaced with a visible light source and used with these new materials.

The organic photocatalysts and/or n-type semiconductor particles will be delivered to the teeth, gums, and tongue by way of a dentifrice containing the photocatalysts along with conventional dentifrice ingredients. Alternatively, the photocatalysts may be delivered in a separate solution, emulsion, or paste which is applied directly to the surface to be treated (e.g., the tongue, gums, etc.) with an application pad or brush, or as a spray, in a mouth wash, or incorporated into a tooth polishing paste. Currently, the most effective n-type semiconductor known for photocatalytic destruction of organic matter is titanium dioxide, which is an n-type material that shows unusually high photoactivity and stability. The anatase crystalline phase is thought by many to be particularly preferred. Other examples of useful photocatalytic semiconductors are n-type semiconductors having a similar photoelectric effect such as zinc oxide, cadmium sulfide, cadmium selenide, strontium titanate, aluminum oxide and zirconium oxide. Among these n-type semiconductors, titanium dioxide is currently preferred n-type semiconductor for this application. Furthermore, it should be noted that $TiO_2$ particles that have been coated to prevent chalking in paint applications should not be used since their photocatalytic functionality will be severely limited by the anti-chalking coating. Among photocatalytic organic agents that have been used are the eosin yellow and methylene blue dyes, sometimes used for infection control and/or tissue crosslinking. For example, when methylene blue dye and $TiO_2$ particles are combined, the efficacy of the UVA-induced photocatalytic process will be visually revealed by the transition of the color of the surface from blue to clear and transparent as the dye is photobleached.

An exemplary dentifrice might contain a fluoride source, a humectant, water, a polishing agent, a thickener, and $TiO_2$. The dentifrice should contain at least about 0.05% to about 1.5% by weight, and preferably from about 0.05% to about 0.5% by weight of an n-type semiconductor approved for use in the mouth. Examples of dentifrices appear in U.S. Pat. Nos. 5,427,770; 5,538,715; 5,686,064; and 5,728,756. It is presently preferred when using $TiO_2$ that this material be present at a level of from about 0.1% to about 1.5% by weight, and preferably that it be present at a level of from about 0.2% to about 0.5% by weight. A mouthwash would contain similar levels of the photocatalyst.

EXAMPLES

The following examples are intended to illustrate the practice of the present invention. These examples are not intended to be exhaustive or limiting of the invention.

Example 1

A patient is provided with a toothbrush as illustrated in FIGS. 2–4, and a dentifrice containing about 0.5% by weight $TiO_2$. The level of viable select deleterious bacteria present in the mouth of the patient is determined. Then, the patient applies the dentifrice to the bristles in the brush head, turns on the UVA light, and begins brushing the teeth, gums, and tongue, after which he rinses with water. After the patient has completed brushing, the brush is turned off and put away, and the level of the same deleterious bacteria in the mouth is measured. The level of viable bacteria in the mouth would be expected to be substantially reduced from that present before the brushing. The level of viable deleterious bacteria on the brush bristles is also measured for comparison purposes later in the example.

On another day, the same patient performs the same procedure using the same dentifrice, brushing for the same length of time, etc.; again the bacterial levels in the mouth are measured before and after brushing, except that the UVA light is not turned on during the brushing procedure. In this test, the level of viable deleterious bacteria in the mouth would be reduced, but substantially less so than when the UVA light is used and compared to that found above. The viable deleterious bacteria on the brush would be expected to be significantly greater than that found in the bristles when the UVA light was used.

Finally, a toothbrush in accordance with U.S. Pat. No. 6,343,400 (discussed above) is used by the patient to perform the same procedure using the same dental dentifrice, brushing for the same length of time, etc., with the bacterial levels in the mouth measured before and after brushing. In this test, the level of viable deleterious bacteria in the mouth would be reduced when using the toothbrush of the '400 patent, but the reduction would be substantially less than that achieved with the toothbrush of FIGS. 2–4.

On another day, the same patient performs the same procedure using the same dentifrice, brushing for the same length of time, etc.; again the bacterial levels in the mouth are measured before and after brushing, except that the UVA light is not turned on during the brushing procedure. In this test, the level of viable deleterious bacteria in the mouth would be reduced, but less so than when the UVA light is used and compared to that found above. The viable deleterious bacteria on the brush would be expected to be significantly greater than that found in the bristles when the UVA light was used.

Example 2

A patient is provided with a flossing device as illustrated in FIGS. 14 and 15, as well as a mouthwash containing $TiO_2$ particles. The patient rinses their mouth with the mouthwash, and then picks up and turns on the flossing device, proceeds to run the length of floss affixed in the head of the device between their teeth. The UVA light provided contiguously to the head of the device in which the floss is mounted irradiates the areas of the mouth past which the flossing device is passed. If the deleterious bacteria in those areas were measured before and after flossing, the level of viable deleterious bacteria would be found to be substantially reduced after flossing with the device.

Example 3

In this example, a dental handpiece as shown in FIG. 17 is used by a dentist. The dental handpiece has a cutting bur and a water source which cools the bur as it is operated by the dentist in removing decayed tooth areas before applying a filling. $TiO_2$ particles are suspended in the water provided by the handpiece, as it is operated. The UVA light source is also turned on while the device is operated. If the level of deleterious bacteria in the mouth and in the portions of the tooth remaining after removal of the decayed matter were measured, it would be found that the level of viable bacteria would be substantially reduced by the application of the $TiO_2$-containing water in conjunction with the direct UVA activation.

Example 4

In this example, a toothbrush in accordance with the present invention as illustrated in FIG. 6 is used and compared to a toothbrush in accordance with U.S. Pat. No. 6,343,400 in regard to bleaching of a patient's teeth. Two corresponding areas of the patient's mouth are identified as areas A and B by drawing an imaginary line between the two front teeth on the top and the bottom of the mouth. The toothbrush of FIG. 6 is used for one month, exclusively in cleaning the teeth in area A. The teeth in area B are cleaned for the same period of time using a toothbrush in accordance with the '400 patent under otherwise identical conditions; the same $TiO_2$-containing dentifrice is used with both brushes.

If the teeth in areas A and B are examined after the one month period, it would be found that the teeth in area A (cleaned with a toothbrush in accordance with the present invention providing direct UVA activation) would be substantially whiter and hence more effectively bleached than the teeth of area B.

Various changes and modifications to the present invention may be made by those of ordinary skill in the art without departing from the spirit and scope of the present invention which is set out in more particular detail in the appended claims. Furthermore, those of ordinary skill in the art will appreciate that the foregoing description is by way of example only, and is not intended to be limiting of the invention as described in such appended claims.

What is claimed is:

1. The toothbrush for delivering UVA light including a head at its distal end and a grip at its proximal end comprising:

a field of tufts of bristles mounted to the top surface of the head; and a direct UVA light source located contiguously to the head, the UVA light source protruding from the surface of the head and being positioned above the surface of the head and below the tips of the tufts of bristles.

2. The toothbrush for delivering UVA light of claim 1 in which the UVA light source is an LED.

3. The toothbrush for delivering UVA light of claim 1 in which the UVA light source is a mercury-xenon bulb.

4. The toothbrush for delivering UVA light of claim 1 in which the UVA light source is mounted in the center of the top of the toothbrush head, surrounded by the tufts of bristles.

5. The toothbrush for delivering UVA light of claim 1 in which the UVA light source comprises LEDs mounted in the toothbrush head generally along its central longitudinal axis, surrounded by the tufts of bristles.

6. The toothbrush for delivering UVA light of claim 1 in which the head is generally rectangular and the UVA light source comprises up to four UVA light sources are located at the corners of the head, outside of the field of the tufts of bristles.

7. The toothbrush for delivering UVA light of claim 1 in which the UVA light source is located at the distal end of the head.

8. The toothbrush for delivering UVA light of claim 1 in which the UVA light source is located at or adjacent to the proximal end of the head.

9. A toothbrush for delivering UVA light including a head at its distal end and a grip at its proximal end comprising:

a field of tufts of bristles mounted to the top surface of the head;

the bristles being mounted by hot melt insertion to form a generally unitary ball at the proximal ends of the bristles, and the ball being contiguous to the UVA light source; and a direct UVA light source located contiguously to the head directly under at least one of the tufts of bristles.

* * * * *